US012685611B2

(12) United States Patent　(10) Patent No.: US 12,685,611 B2
Dacus et al.　(45) Date of Patent: Jul. 21, 2026

(54) SELF-BIASING ANKLE CLAMP TIBIAL ALIGNMENT GUIDE

(71) Applicant: Joint Development, Inc., Salt Lake City, UT (US)

(72) Inventors: Eric M. Dacus, Salt Lake City, UT (US); Luca Terziotti, Salt Lake City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 584 days.

(21) Appl. No.: 17/973,372

(22) Filed: Oct. 25, 2022

(65) Prior Publication Data

US 2023/0128714 A1　Apr. 27, 2023

Related U.S. Application Data

(60) Provisional application No. 63/272,623, filed on Oct. 27, 2021.

(51) Int. Cl.
　*A61B 17/15*　(2006.01)
　*A61B 90/57*　(2016.01)
(52) U.S. Cl.
　CPC ............ *A61B 90/57* (2016.02); *A61B 17/157* (2013.01); *A61B 2090/571* (2016.02)
(58) Field of Classification Search
　CPC .. A61B 90/57; A61B 17/157; A61B 2090/571
　USPC .................................... 606/87–88; 623/21.18
　See application file for complete search history.

(56) References Cited

U.S. PATENT DOCUMENTS

| | | | | |
|---|---|---|---|---|
| 5,002,547 | A | * | 3/1991 | Poggie .................... A61F 2/461 606/88 |
| 5,197,944 | A | * | 3/1993 | Steele .................. A61B 17/157 606/86 R |
| 5,250,050 | A | * | 10/1993 | Poggie ............... A61B 17/1677 606/88 |
| 6,221,035 | B1 | * | 4/2001 | Kana .................... A61B 17/157 606/88 |
| 11,497,509 | B2 | * | 11/2022 | Hirt ...................... A61B 17/645 |
| 2004/0015173 | A1 | * | 1/2004 | Irving .................. A61B 17/157 606/88 |
| 2005/0143746 | A1 | * | 6/2005 | Steffensmeier ...... A61B 17/157 606/88 |
| 2006/0241639 | A1 | * | 10/2006 | Kuczynski ........... A61B 17/155 606/88 |
| 2008/0132818 | A1 | * | 6/2008 | Livorsi ................ A61B 17/154 602/23 |

(Continued)

FOREIGN PATENT DOCUMENTS

WO　WO-2021209496 A2 * 10/2021　........... A61B 17/157

*Primary Examiner* — Jessica Weiss
(74) *Attorney, Agent, or Firm* — Lowry Blixseth APC; Scott M. Lowry

(57) ABSTRACT

The self-biasing ankle clamp tibial alignment guide includes a clamp body, at least one lever arm outwardly extending from the clamp body, and an alignment rod generally upwardly extending toward a proximal end of a patient tibia and movable relative to the clamp body. A strap couples to the lever arm to exert a force thereon offset from a contact point where the clamp body pulls into engagement with a patient, thereby generating a moment about the contact point that causes the alignment rod carrying a cutting guide to bias forward into engagement with the patient.

15 Claims, 8 Drawing Sheets

(56)                  References Cited

U.S. PATENT DOCUMENTS

2008/0132897 A1*   6/2008  Livorsi  .................. A61B 90/36
                                                                 606/88
2008/0154270 A1*   6/2008  Haines  ................. A61B 17/155
                                                                 623/20.14
2018/0280031 A1*  10/2018  Fiedler  ............... A61B 17/1764
2022/0015858 A1*   1/2022  Dubois  .................. A61B 90/39

* cited by examiner

SELF-BIASING ANKLE CLAMP TIBIAL ALIGNMENT GUIDE

BACKGROUND OF THE INVENTION

The present invention generally relates to a self-biasing ankle clamp tibial alignment guide. More specifically, the self-biasing ankle clamp tibial alignment guide may include a strap offset from a clamp body by a lever arm, whereby exerting a force at the point where the strap engages the lever arm generates a moment about a contact point where the clamp body is drawn into engagement with a patient leg, thereby self-biasing an alignment rod toward the leg of a patient without the need for the surgeon to manually hold the alignment rod adjacent the patient leg.

During knee arthroplasty, the proximal end of a patient tibia is resurfaced before affixing a knee replacement tibial component to the bone. The resurfacing process requires resecting the damaged portion of the tibial bone and carti-lage. The amount of bone, cartilage, and other organic material resected depends on the extent of the damage, anatomy of the patient, and size of the knee replacement components. If precise cuts are not made during the resect-ing step, the tibial component may not sit on the tibial bone properly and be misaligned with the rest of the knee replace-ment components. As such, tibial cutting guides are used to ensure precise cuts. One method of aligning the cutting guide to the tibia involves drilling an intramedullary canal into the proximal end of the tibia, mounting an alignment guide within the hollowed out intramedullary canal, and positioning the cutting guide adjacent to the proximal end of the tibia via the alignment guide. This process is time consuming, and drilling the intramedullary canal into the proximal end of the tibia increases the intrusiveness of the knee arthroplasty.

Another method for aligning the cutting guide utilizes extramedullary alignment guides that attach to the outside of the patient leg. One such device is an ankle bracket align-ment guide that clamps onto the distal end of the patient tibia and extends towards the proximal end. The cutting guide is then positioned at the proximal end of the tibia and held in place during cutting. The guide is either held in place manually or affixed to the tibia via pins inserted into the anterior of the bone. Example prior art devices are shown and described, e.g., in U.S. Pat. Nos. 5,197,944 and 6,221,035, the contents of which are herein incorporated by reference in their entireties. While existing extramedullary devices decrease the intrusiveness of aligning the tibial cutting guide, residual problems remain. The mass of the cutting guide at the proximal end of the extramedullary alignment guide causes the cutting guide to tip away from the leg or otherwise fall out of alignment. Therefore, a surgeon or surgical assistant must manually resist the mass of the cutting guide to prevent tipping while cuts are made, or at least until the cutting guide is affixed to the bone.

While the surgeon is manually preventing the cutting guide from tipping, they are hindered from carrying out other tasks required during the procedure. For example, the surgeon may have to hold the cutting guide in place with one hand and locate the bone saw, or other surgical equipment with the other. If a surgical assistant is required to manually resist the mass of the cutting guide, the procedure space becomes crowded and inconvenient. Similarly, the surgical assistant is then inhibited from performing other duties required by procedure. Furthermore, the alignment process may require loosening and retightening the alignment guide to make cut orientation adjustments. During this loosening and/or retightening step, the surgeon or surgical assistant may have to manually prevent tipping. Any tendency for the cutting guide to tip away from the tibia increases the possibility of improper placement and cuts. This may lead to incorrect alignment of the tibial component and knee replacement as a whole.

There exists, therefore, a significant need for a self-biasing ankle clamp tibial alignment guide that includes a clamp body, a clamp arm coupled to the clamp body, a lever arm coupled to the clamp arm, an alignment rod coupled to the clamp body and generally upwardly extending toward the proximal end of a patient tibia, and a strap coupled to the lever arm, wherein the strap is offset from a contact point where the clamp body engages a patient leg by a height of the lever arm, thereby generating a moment about the contact point that self-biases and self-aligns the alignment rod relative to the patient leg. The present invention fulfills these needs and provides further related advantages.

SUMMARY OF THE INVENTION

In one embodiment disclosed herein, an ankle clamp tibial alignment guide may include a clamp body having a patient-contacting interface selectively engageable with an ankle of a patient, a rod upwardly extending from the clamp body terminating in a cutting guide end selectively coupled with a cutting guide distal from the patient-contacting interface, and a strap selectively coupled to a lever arm extending from the clamp body and positioned relative to the patient-contacting interface to, upon tightening, generate a moment near where the patient-contacting interface selectively engages the ankle, to self-bias the cutting guide end of the rod generally toward the patient.

More specifically, the patient-contacting interface may include a pair of outwardly extending clamp arms having an arcuate shape that forms a U-shaped or Y-shaped enclosure for selectively receiving the ankle of a patient therein. In this embodiment, the lever arm may be a pair of lever arms that each upwardly extend from the pair of outwardly extending clamp arms. Here, opposite ends of the strap may couple to respective distal ends of the lever arms to be positioned relatively higher than the patient-contacting interface selec-tively engageable with the ankle. In alternative embodi-ments, the lever arm may be extendable and/or the rod may be a selectively adjustable telescoping rod.

In another alternative embodiment, the lever arm may be a lower rod-integrated lever arm formed from a portion of and coaxial with the upwardly extending rod. Here, the strap may selectively couple to opposite sides of the lower rod-integrated lever arm below an upper alignment post, to self-bias the upper alignment post generally toward the patient about the moment.

Moreover, the clamp body may further include a casing housing a slide integrated therewith for selectively horizon-tally positioning the patient-contacting interface and the rod relative to the patient. Here, the casing may include an externally accessible lock movable between a first unlocked position permitting movement of the slide relative to the casing and a second locked position in friction fit engage-ment with the slide thereby inhibiting movement of the slide relative to the casing. Moreover, a hinge may couple the rod to the clamp body to permit pivoting movement of the rod relative to the clamp body. Additionally, the strap may include a first end selectively adjustably couplable with one of the pair of lever arms by way of a series of apertures formed within the strap and a second end selectively adjust-ably coupled with the other of the pair of lever arms by a selectively lockable adjustment housing. The strap may be selected from the group consisting of an elastic strap, a rubber strap, a silicone strap, a plastic strap, a belt, and a metal spring. Alternatively, the strap may be a pair of spring-loaded clamping paddles positioned along the lever arm.

In an alternative embodiment, a process for aligning a tibial cutting guide with an ankle clamp as disclosed herein may include steps for positioning a lower patient-contacting interface of the ankle clamp for select engagement with an ankle of a patient, wrapping a strap coupled to an outwardly extending lever arm of the ankle clamp around the ankle of the patient, and tightening the strap to draw the lower patient-contacting interface into engagement with the ankle to generate a moment thereon self-biasing a cutting guide end of a rod upwardly extending from the ankle clamp carrying the tibial cutting guide generally toward to patient. The tightening step may also include the step of coupling at least one of a plurality of apertures formed at one end of the strap to a knob and threading an opposite end of the strap in select lockable relation within an adjustment housing.

In an alternative aspect of these embodiments, the length of the upwardly extending rod may be telescopingly adjusted, the tibial cutting guide may be adjustably coupled to the cutting guide end of the rod in locking engagement thereto, and the rod may be pivoted relative to the clamp body about a hinge, such as side-to-side and/or forward/rearward. Moreover, the knob and the adjustment housing may couple to opposite sides of the lever arm and the process may further include the step of generally horizontally positioning the upwardly extending rod relative to the patient with a selectively adjustable slide.

Additionally, the positioning step may further include the step of aligning the ankle of the patient within a U-shaped enclosure forming the patient-contacting interface. Here, the U-shaped enclosure may include a pair of outwardly extending arcuate clamp arms and the lever arm may include a pair of lever arms upwardly extending from each of the pair of outwardly extending arcuate clamp arms. In this embodiment, the strap may selectively couple to each of the pair of lever arms.

In accordance with another embodiment, an ankle clamp tibial alignment guide may include a clamp body, at least one clamp arm outwardly extending from the clamp body, and a lever arm upwardly extending from the at least one clamp arm. The ankle clamp tibial alignment guide may further include an alignment rod coupled to the clamp body and generally upwardly extending toward a proximal end of a patient tibia. A strap may couple to the lever arm to exert a force thereon offset from a contact point where the clamp body is pulled into engagement with a patient leg, thereby generating a moment about the contact point that causes the alignment guide to bias toward the patient leg.

In another embodiment, the at least one clamp arm may be a pair of clamp arms outwardly extending from the clamp body. The pair of clamp arms may be arcuate clamp arms configured to receive the patient leg and form a three-sided enclosure such as a Y-shape or U-shape enclosure. Moreover, the at least one lever arm may be a pair of lever arms with a first lever arm coupled to a first clamp arm and a second lever arm coupled to a second clamp arm. Here, the length of the first and/or second arms may be adjustable. In other embodiments, the first lever arm may include an outwardly extending knob capable of engaging the strap by way of an aperture or the like and the second lever arm may include an adjustment housing that may allow select locking adjustment of the strap therein. For example, the adjustment housing may include a clamp that locks the strap to a desired length, which may range from a half inch to eight inches.

Additionally, the clamp body may further include a slide for moving the alignment rod coupled thereto relative to the clamp body. The alignment rod may couple to the slide about a casing that includes a locking mechanism, such as a brake-style lock. Moreover, the strap may be an elastic strap, rubber strap, silicone strap, plastic strap, or any other suitable material known in the art. In alternative embodiments, the strap may be a belt or metal spring, or the strap may be a pair of clamping paddles with a first clamping paddle coupled to the first lever arm and a second clamping paddle coupled to the second lever arm. The strap may also detachably couple to at least one or both of the lever arms such as by way of the knob, the apertures, adjustment housing, or another adjustable or non-adjustable attachment mechanism known in the art.

In alternative embodiments, the alignment rod may be hingedly coupled to the clamp body, slide arm, or casing, thereby allowing the alignment rod to pivot (e.g., left/right and/or forward/rearward) for alignment with the patient leg. Such forward/rearward movement may allow the alignment rod to pivot away from the patient leg after a tibial cutting guide is affixed to the proximal end of the tibia. The alignment rod may be a telescoping rod adjustable in length and include a lock for retaining the telescoping rod at a specific (desired) length. The alignment rod may also be configured to couple with a tibial cutting guide in slidable engagement therewith. In this respect, a lock may retain the tibial cutting guide in a position relative to the alignment rod once the tibial cutting guide is adjacent the proximal end of the patient tibia. Lastly, at least one of the clamp body, the clamp arms, the lever arms, and/or the alignment rod may be made out of a metal material (e.g., stainless steel, aluminum, titanium, or the like) or a plastic material such as a biocompatible high-density plastic material (e.g., polypropylene, polyethylene, or the like).

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 4:
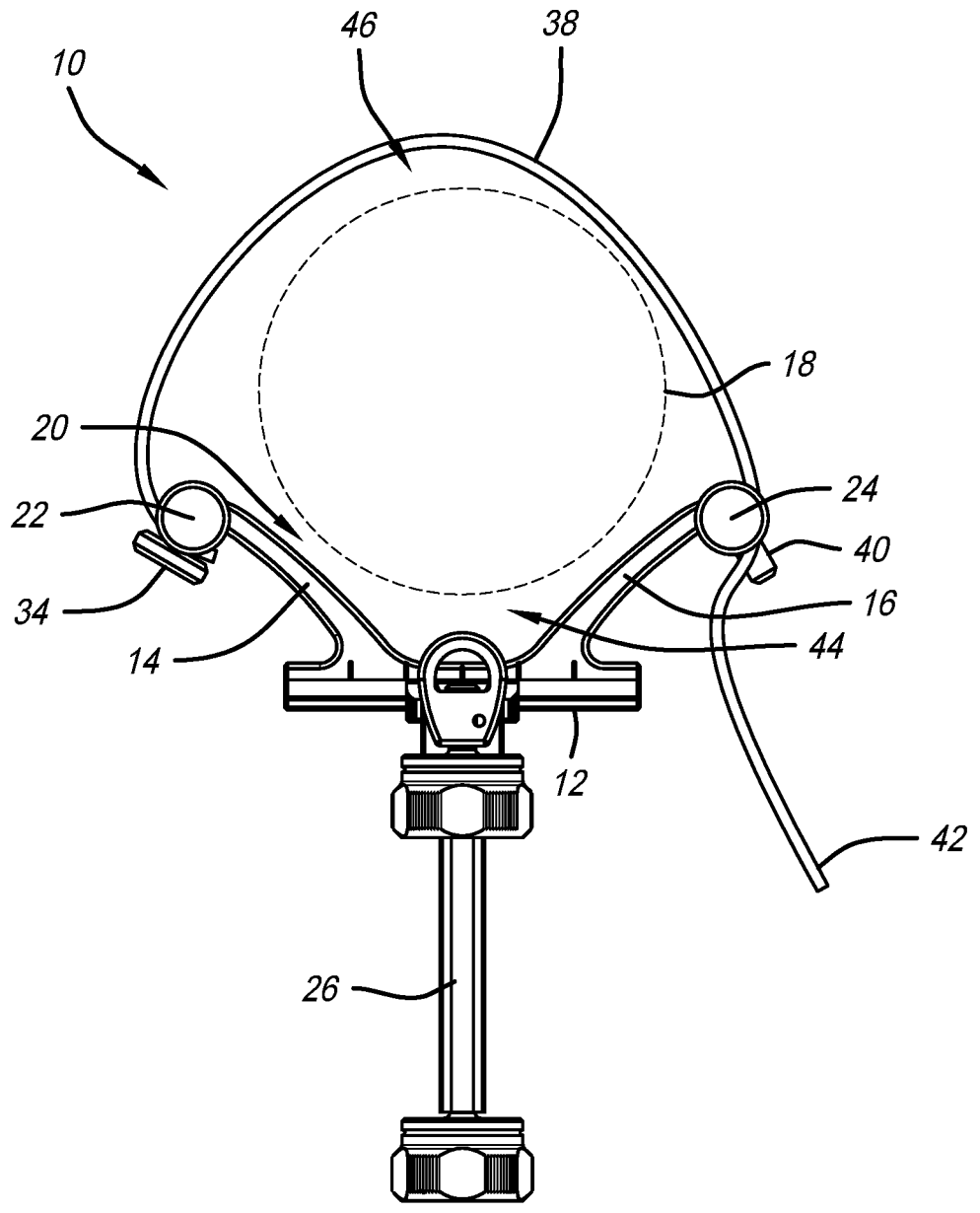
FIG. 4 is a top plan view of the ankle clamp tibial alignment guide disclosed herein.
Figure 5:
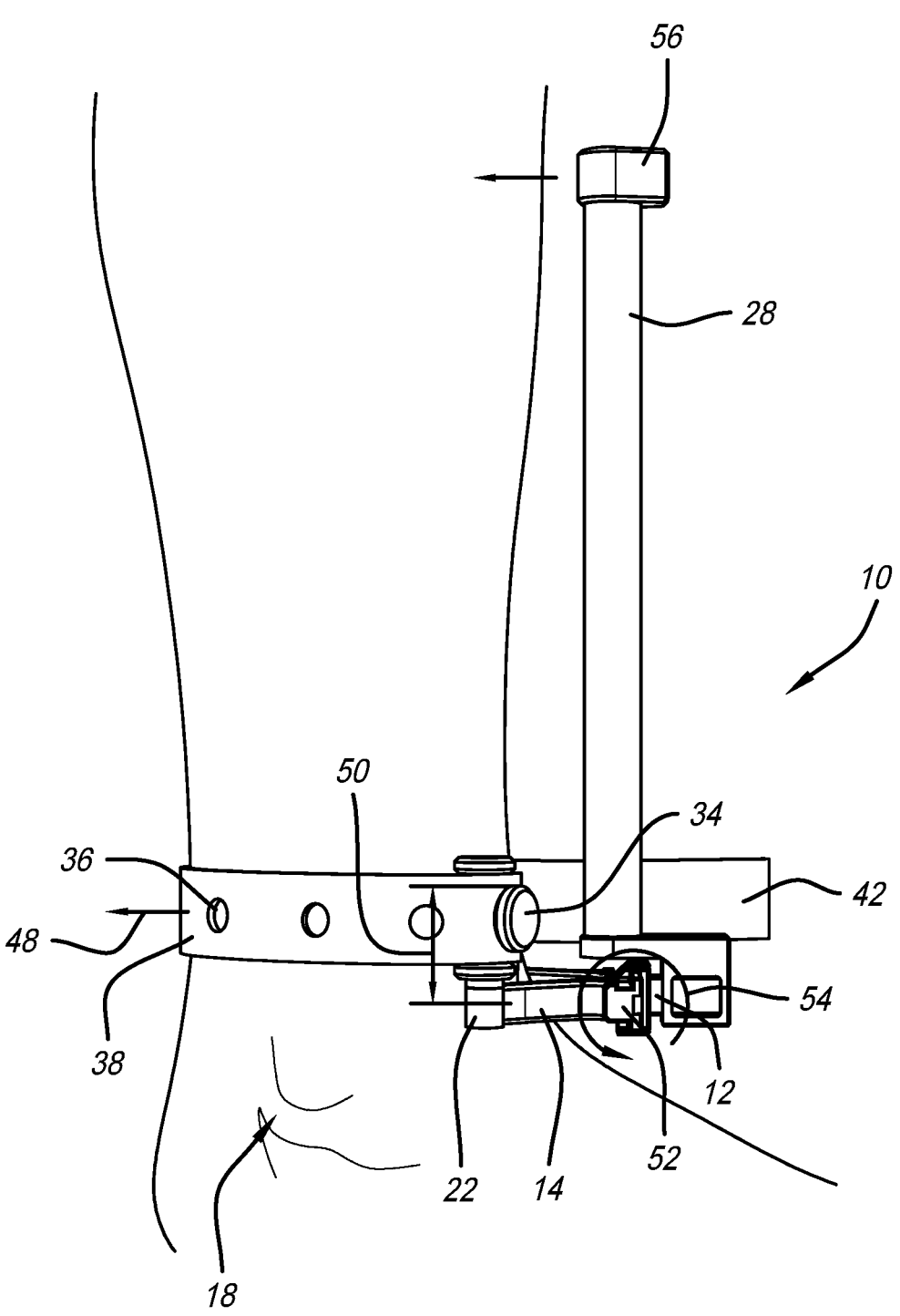
FIG. 5 is an environmental perspective view of the ankle clamp tibial alignment guide of FIGS. 1-4 coupled to a patient leg.
Figure 6:
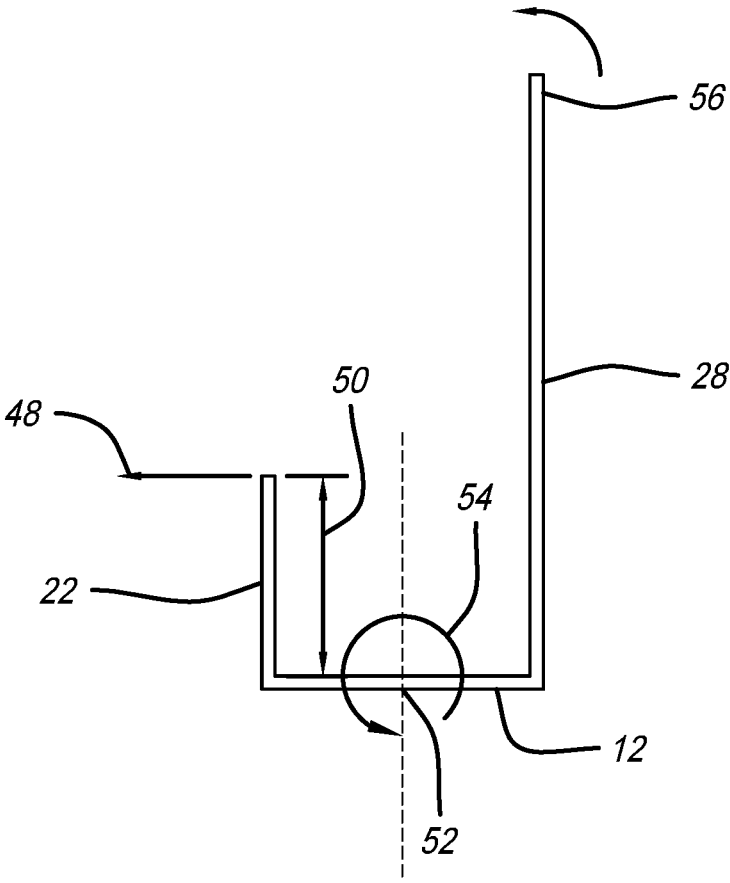
FIG. 6 is a free body diagram of the ankle clamp tibial alignment guide of FIGS. 1-5.

As shown in the exemplary drawings for purposes of illustration, the present invention for an ankle clamp tibial alignment guide is generally illustrated in FIGS. 1-5 and 7 with respect to reference numeral 10. As illustrated, the ankle clamp tibial alignment guide 10 may include a clamp body 12 having a first clamp arm 14 and a second clamp arm 16 outwardly extending therefrom that help a surgeon generally locate the clamp body 12 proximate a patient ankle 18, e.g., as illustrated in FIG. 5. As best illustrated in the top plan view of FIG. 4, each of the clamp arms 14, 16 respectively generally curve outwardly from each side of the clamp body 12 to generally form a three-sided enclosure 20 conducive for enclosing the patient ankle 18 therein. FIG. 5 illustrates that the enclosure formed by the clamp body 12 and the outwardly arcing structure of the clamp arms 14, 16 is relatively wider at the opening, e.g., near where a first lever arm 22 and a second lever arm 24 couple to each of the respective first and second clamp arms 14, 16, and generally arcuately converge toward the clamp body 12. As such, even if the patient ankle 18 is misaligned upon entry within the enclosure 20, the ankle 18 will slide along the arcuate structure of either of the first clamp arm 14 or the second clamp arm 16 into a central portion of the clamp body 12 near where a slide rod 26 extends therefrom. A generally upstanding alignment rod 28 couples to the slide rod 26 about a casing 30 having a lock 32 integrated therewith. As such, a surgeon can selectively position the alignment rod 28 along the length of the slide rod 26 by way of the sliding interaction of the casing 30 relative thereto. Moreover, once in place, e.g., near the patient ankle 18 and near a proximal end of the patient tibia, the alignment rod 28 may be locked in place along the length of the slide rod 26 by the lock 32 integrated with the casing 30. The lock 32 may simply be a brake-style locking mechanism, namely one that engages the slide rod 26 to frictionally resist movement of the casing 30 retaining the alignment rod 28 away from the patient ankle 18 during surgery.

Figure 1:
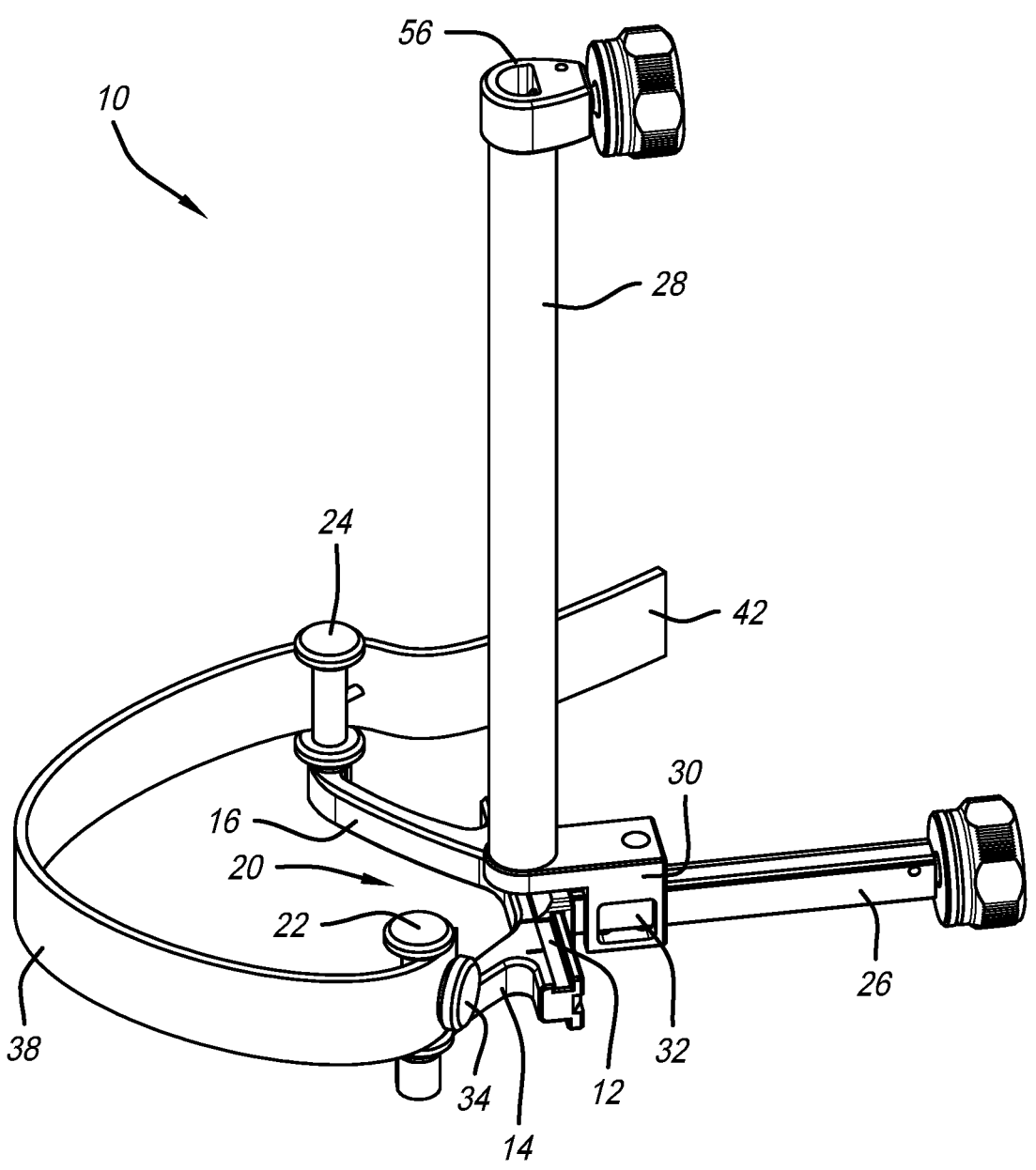
FIG. 1 is a perspective view of an exemplary embodiment of an ankle clamp tibial alignment guide disclosed herein.
Figure 2:
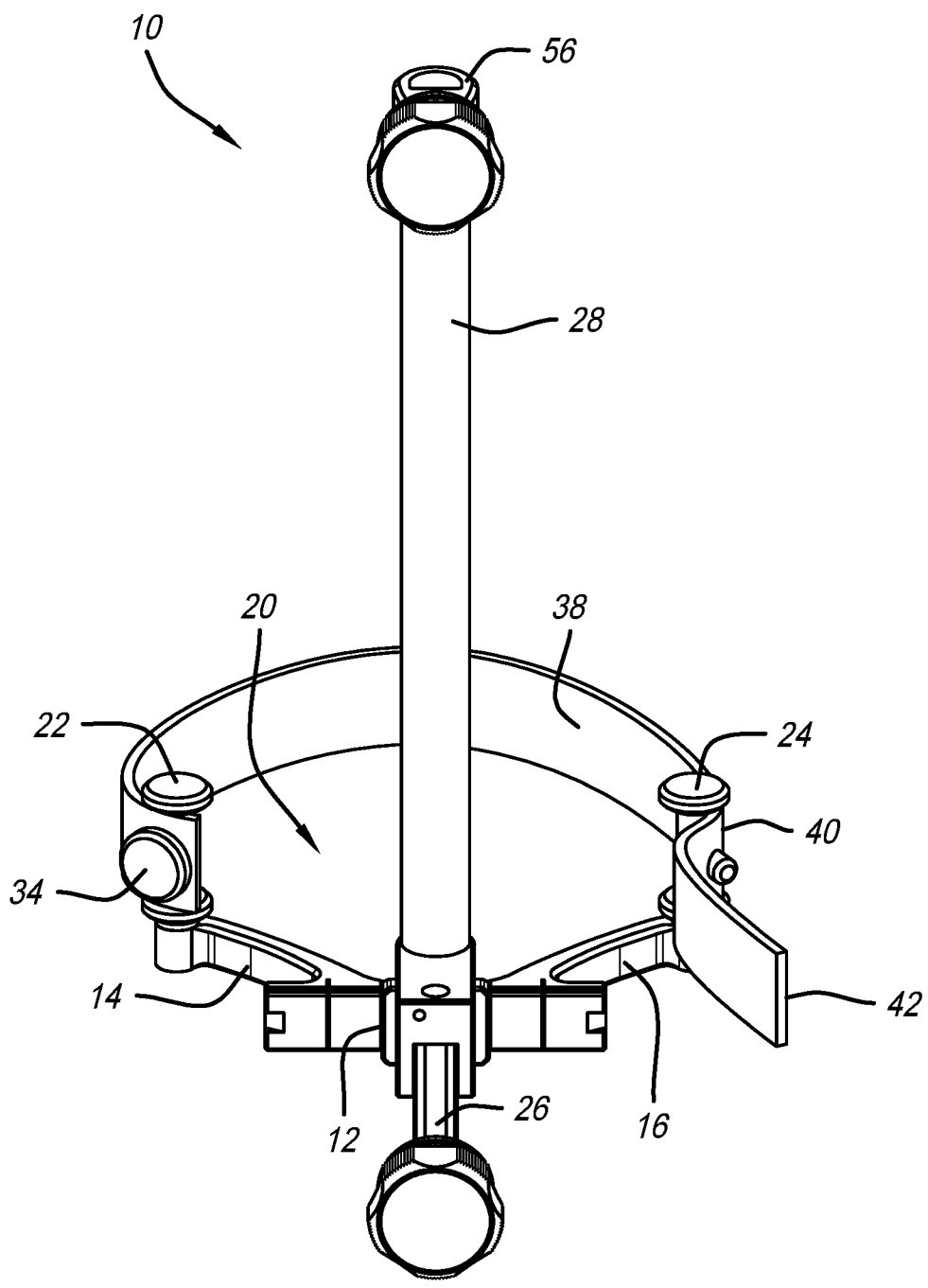
FIG. 2 is an anterior perspective view of the ankle clamp tibial alignment guide disclosed herein.
Figure 3:
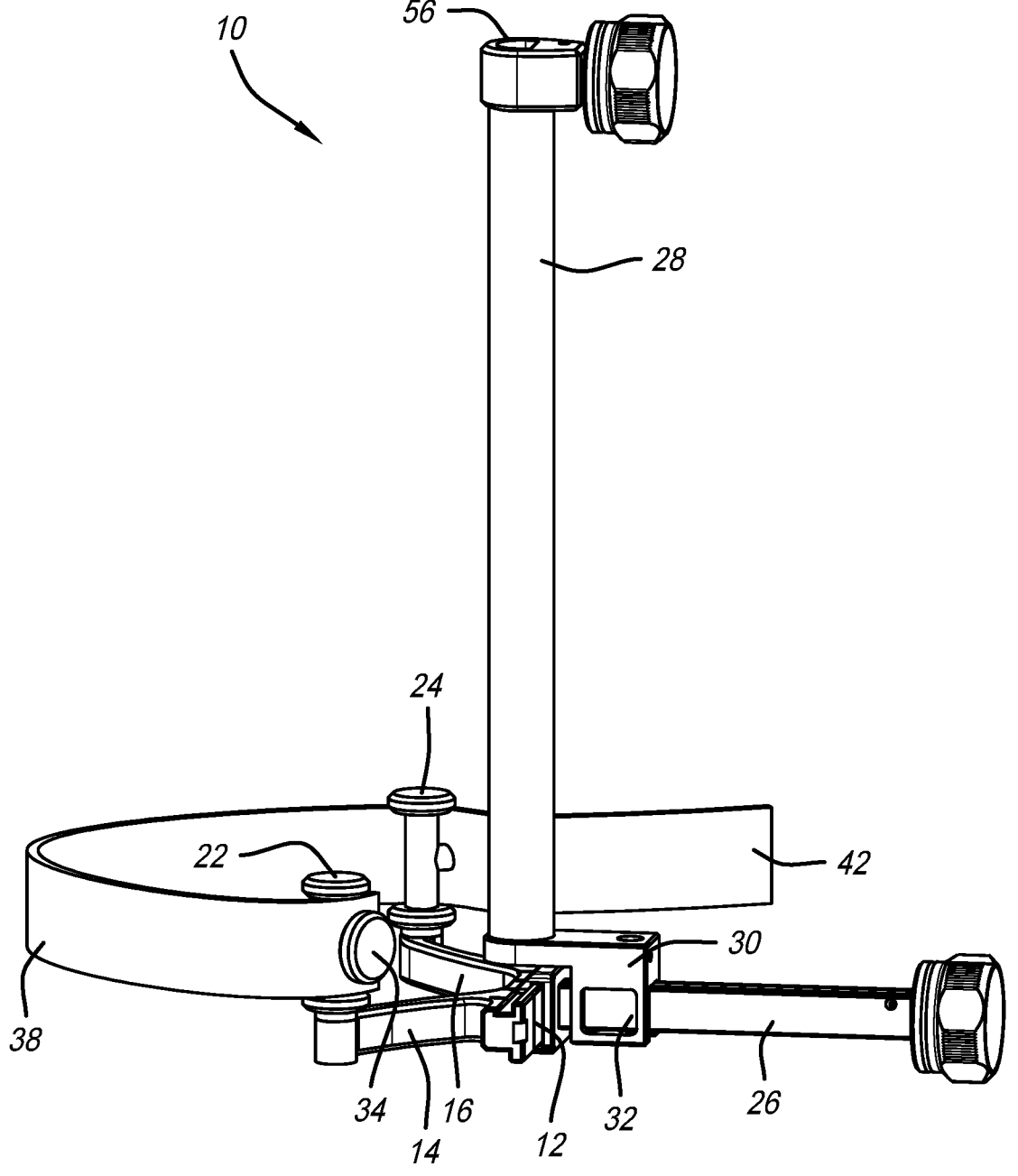
FIG. 3 is a side perspective view of the ankle clamp tibial alignment guide disclosed herein.

As best illustrated in FIGS. 1-3 and 5-6, each of the first lever arm 22 and the second lever arm 24 are positioned at a distal end of each of the respective first and second clamp arms 14, 16 and are generally upwardly extending therefrom, thereby effectively creating a moment arm relative to the first and second clamp arms 14, 16, as discussed in more detail below. As illustrated herein, the first lever arm 22 further includes an outwardly projecting knob 34 having a size and shape for select reception of one of a set of apertures 36 formed along a length of a strap 38, e.g., as illustrated best in FIG. 5. Here, the strap 38 is illustrated as an elastic band having a length sufficient to extend around an exterior perimeter of the patient ankle 18 for coupling with an adjustment housing 40 (FIGS. 2 and 4). A free end 42 of the strap 38 may pull through the adjustment housing 40 for purposes of setting the desired length of the strap 38 that extends around the patient ankle 18. Once at the desired position, the adjustment housing 40 may clamp to the strap 38 to substantially retain the strap 38 at the desired length around the patient ankle 18. Such adjustment allows the strap 38 to accommodate ankles 18 having different sizes. Additional adjustment of the length of the strap 38 may also be accomplished by threading the knob 34 into a different aperture 36 along the length of the strap 38. That is, threading the knob 34 through one of the apertures 36 closer to the free and 42 of the strap 38 will effectively decrease the size of the strap 38 able to wrap around a portion of the patient ankle 18 as disclosed herein, and vice versa.

In operation, and as best illustrated in FIG. 4, a surgeon may locate the clamp body 12 and the first and second clamps arms 14, 16 around an anterior portion 44 of the of the patient ankle 18 and then extend the strap 38 around a posterior portion 46 of the patient ankle 18. The free end 42 of the strap 38 threads through the adjustment housing 40 and can then be pulled tight therein, thereby exerting a force 48 at the point where the strap 38 couples to the first lever arm 22 at the knob 34. The force 48 is offset from the clamp body 12 by a distance 50 (FIGS. 5 and 6) governed by the height of the lever arms 22, 24. This effectively draws the anterior portion 44 of the clamp body 12 into engagement with the patient ankle 18 at a contact point 52. As a consequence, the force 48 applied along the first clamp arm 14 is relatively higher than the contact point 52, thereby creating a moment 54 about the contact point 52 that causes the entire ankle clamp tibial alignment guide 10 to rotate forward into the anterior portion 44 of the patient ankle 18. Moreover, the moment 54 also rotates or biases a proximal end 56 of the alignment rod 28 toward the patient. Therefore, the mass of the cutting guide that couples thereto will not cause the ankle clamp tibial alignment guide 10 to fall away from the patient; rather, the moment 54 causes the ankle clamp tibial alignment guide 10 to rotate forward into engagement with the patient. This makes it easier for the surgeon to fix the cutting guide (not shown) to the patient, including in instances where the alignment process may require loosening and retightening surgical equipment to make cut orientation adjustments. In one embodiment, the length of the lever arms 22, 24, and therefore the distance 50, may range from 0.5 to 8 inches. As the moment arm increases in length, the moment 54 created by the force 48 also increases. In one embodiment, the lever arms 22, 24 may be extendable so that the surgeon may set the length of the lever arms 22, 24 and the corresponding distance 50 to attain the desired moment 54 for positioning the ankle clamp tibial alignment guide 10 relative to the patient as desired.

The force 48 may be a clamping force or a tension force depending on the type of the strap 38. For example, if the strap 38 is an elastic strap, the force 48 may be created by tightening the strap 38 around the posterior portion 46 of the patient ankle 18, as briefly discussed above. Of course, the strap 38 may also be a rubber strap, silicone strap, plastic strap, or any other suitable strap known in the art to retain the ankle clamp tibial alignment guide 10 relative to the patient ankle 18. Alternatively, the strap 38 may be a belt or metal spring. In these embodiments, the strap 38 may detachably couple to at least one or both of the lever arms 22, 24, such as by way of the knob 34, the apertures 36, or another adjustable or non-adjustable attachment mechanism as may be known in the art. In alternative embodiments, the strap 38 may be a pair of clamping paddles, with a first clamping paddle coupled to the first lever arm 22 and a second clamping paddle coupled to the second lever arm 24. The clamping paddles may be spring loaded and exert a clamping force to generate the moment 54 about the contact point 52.

In another embodiment, the alignment rod 28 may be an extendable telescoping rod. Such a telescoping feature enables the surgeon to adjust the length of the alignment rod 28 according to the length of the patient ankle 18. The telescoping rod 28 may include a locking mechanism to lock the alignment rod 28 at a desired length. In an alternative embodiment, the alignment rod 28 may allow slidable engagement with a tibial cutting guide (not shown). A surgeon may slide the tibial cutting guide along the length of the alignment rod 28 to a desired location adjacent the proximal end of the patient tibia. In this embodiment, the ankle clamp tibial alignment guide 10 may have a locking mechanism that secures the ankle clamp tibial alignment guide 10 to the alignment rod 28 and allows the surgeon to lock the ankle clamp tibial alignment guide 10 in place at the desired location.

The alignment rod 28 may also hingedly couple to the clamp body 12 (such as by way of the casing 30) to enable the surgeon to position the alignment rod 28 to the left or to the right of the patient ankle 18. This may be particularly useful if the patient ankle 18 bows in one direction or another. In alternative embodiments, the hingedly coupled alignment rod 28 may allow the surgeon to tip the alignment rod 28 away from the patient ankle 18 after the tibial cutting guide affixes to the proximal end of the patient tibia. In one embodiment, the clamp body 12 may include a locking mechanism to secure the hingedly coupled alignment rod 28 in place after the surgeon positions the alignment rod 28.

In yet another embodiment, the first and second clamp arms 14, 16 may extend to the left and right of the patient ankle 18 in a Y-shape or U-shape configuration with the clamp body 12. This embodiment may increase the amount of contact between the patient ankle 18 and the clamp body 12 (e.g., in a cupping relationship) to improve the overall stability of the ankle clamp tibial alignment guide 10 during the alignment process. Furthermore, the first and second clamp arms 14, 16 may be adjustable, i.e., the first and second clamp arms 14, 16 may initially have a relatively wider width to facilitate insertion of the patient ankle 18 in between, and then adjust to close the gap in between to better cup or hold the patient ankle 18 therein.

In an alternative embodiment, the ankle clamp tibial alignment guide 10 may include only one of the clamp arms 14, 16. Here, the strap 38 may extend circumferentially around the patient ankle 18 for coupling to only one of the first or second lever arms 22, 24 (i.e., the first and second ends of the strap 38 couple to a common lever arm 22, 24). In this embodiment, the strap 38 is still able to exert the force 48 at a position offset from the clamp body 12 by the distance 50, to produce the moment 54 at the contact point 52 for biasing the proximal end 56 of the alignment rod 28 toward the patient during use.

Any of the clamp body 12, the clamp arms 14, 16, the lever arms 22, 24, and/or the alignment rod 28 may be made out of a metal material (e.g., stainless steel, aluminum, titanium, or the like) or may be made out of a plastic or a biocompatible and high-density plastic material (e.g., polypropylene, polyethylene, or the like).

Figure 7:
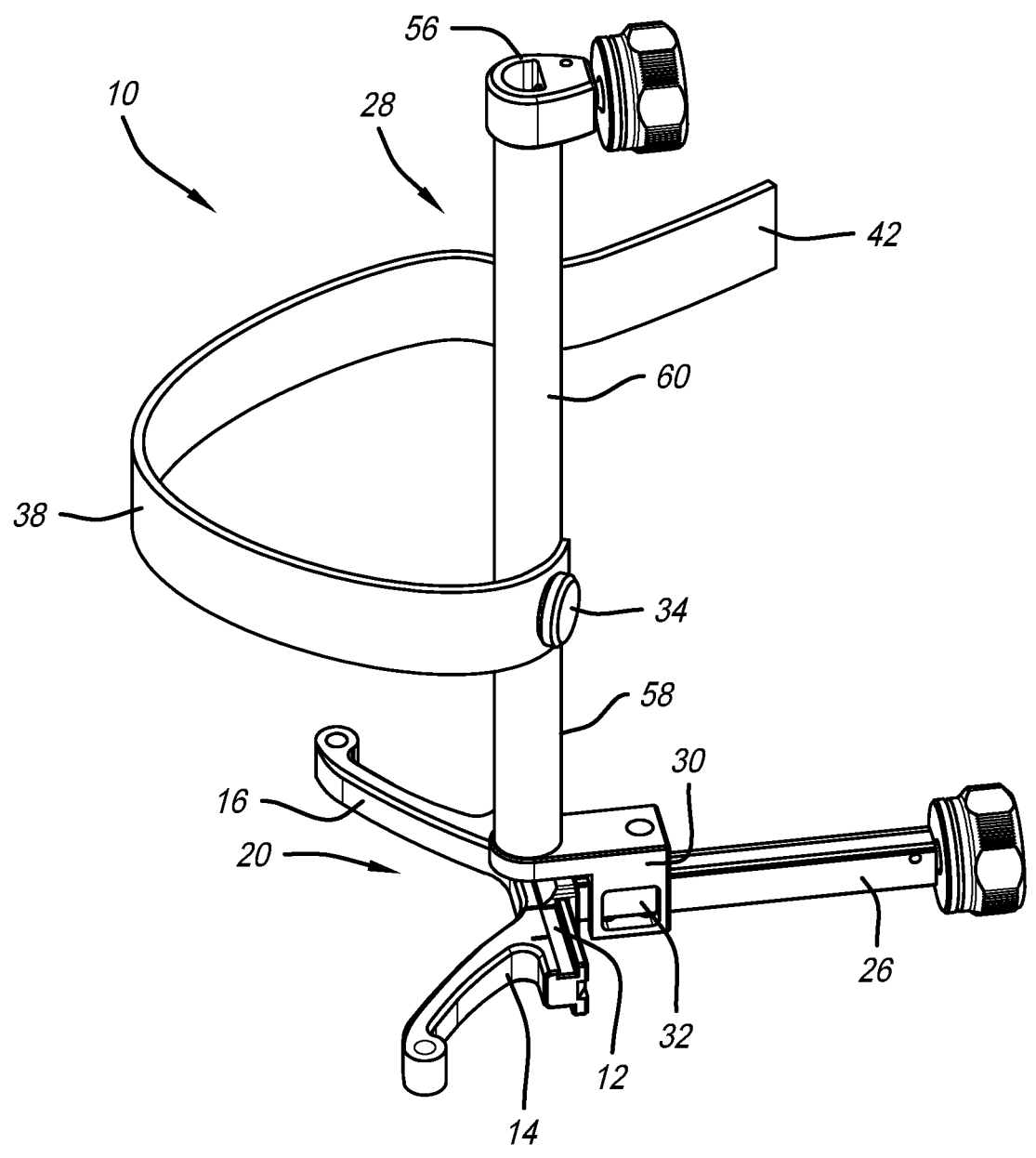
FIG. 7 is a perspective view of an alternative embodiment of the ankle clamp tibial alignment guide wherein the strap connects to a rod-integrated lever arm of an alignment rod.

In another alternative embodiment, as illustrated in FIG. 7, the strap 38 may selectively couple to the alignment rod 28, thereby essentially splitting the alignment rod 28 into a lower rod-integrated lever arm 58 and an upper alignment post 60. Here, the strap 38 couples to an upper end of the rod-integrated lever arm 58 via the knob 34 and is designed to have a length to extend around a posterior portion 46 of the patient ankle 18 (FIG. 4) in a similar fashion as disclosed above. In this embodiment, the adjustment housing 40 (not shown in FIG. 7) may be relocated to a position opposite the knob 34 along the upper end of the rod-integrated lever arm 58 such that the free end 42 of the strap 38 can thread therethrough. This allows for the strap 38 to be pulled tight around the ankle 18 and held in place. Doing so causes forward movement such that the ankle clamp tibial alignment guide 10 is pulled into contact with or otherwise engages the patient ankle 18. This causes the upper alignment post 60 to rotate or rock forward into engagement with the patient in accordance with the embodiments disclosed herein, and as discussed in more detail below with respect to the free body diagram of FIG. 8. In embodiments where the strap 38 includes more than one aperture (e.g., as illustrated in FIG. 5), the length of the strap 38 may be additionally or alternatively adjusted by threading the knob 34 into a different aperture 36 along the length of the strap 38. Of course, the strap 38 may couple to the rod-integrated lever arm 58 by any method disclosed herein or known in the art.

Figure 8:
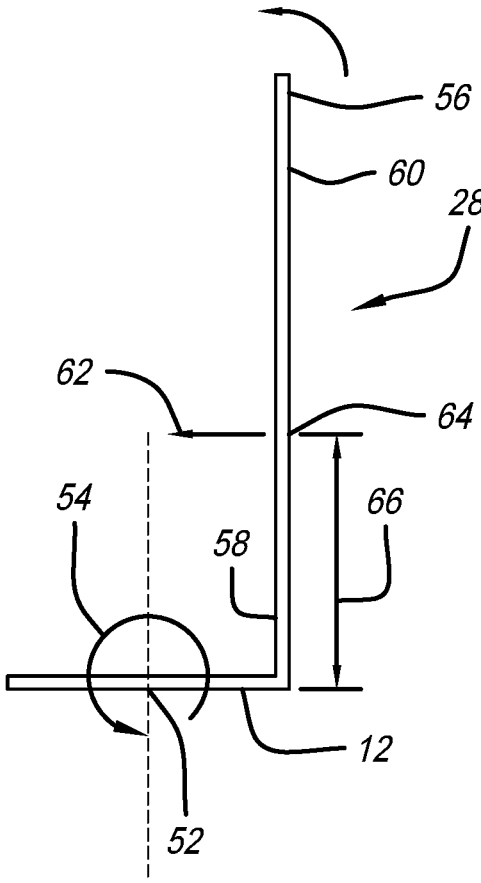
FIG. 8 is a free body diagram of the alternative ankle clamp tibial alignment guide of FIG. 7.

FIG. 8 illustrates a free body diagram of the alternative embodiment of the ankle clamp tibial alignment guide 10 illustrated in FIG. 7, more specifically illustrating the creation of the moment 54 at the contact point 52 where the clamp body 12 contacts the patient ankle 18 when tightening the strap 38 about the rod-integrated lever arm 58. That is, tightening the strap 38 in this respect creates a force 62 at a connection point 64 where the strap 38 couples to the rod-integrated lever arm 58. The force 62 is offset from the clamp body 12 by a distance 66, which is determined by the height of the rod-integrated lever arm 58. This similarly effectively draws the anterior portion 44 of the clamp body 12 into engagement with the patient ankle 18 at the contact point 52. Since the force 62 applied along the rod-integrated lever arm 58 is relatively higher than the contact point 52, doing so creates a similar moment 54 about the contact point 52 that causes the entire alternative ankle clamp tibial alignment guide 10 to rotate forward into the anterior portion 44 (FIG. 4) of the patient ankle 18. Similarly, the moment 54 rotates or biases the proximal end 56 of the upper alignment post 60 toward the patient ankle 18. Unlike the prior art, the mass of the cutting guide that couples thereto will not cause the ankle clamp tibial alignment guide 10 to fall away from the patient ankle 18; rather, the moment 54 again causes the ankle clamp tibial alignment guide 10 to rotate forward into engagement with the patient ankle 18.

Although several embodiments have been described in detail for purposes of illustration, various modifications may be made without departing from the scope and spirit of the invention. Accordingly, the invention is not to be limited, except as by the appended claims.

What is claimed is:

1. An ankle clamp tibial alignment guide, comprising:
   a clamp body having a patient-contacting interface selectively engageable with an ankle of a patient;
   a rod upwardly extending from the clamp body terminating in a cutting guide end distal from the patient-contacting interface; and
   a restraint selectively coupled to at least one lever arm, the at least one lever arm extending up from the clamp body and positioned entirely above the patient-contacting interface, wherein tightening the restraint generates a moment near where the patient-contacting interface selectively engages the ankle, to self-bias the cutting guide end of the rod generally toward the patient.

2. The alignment guide of claim 1, wherein the at least one lever arm upwardly extends from the clamp body and the restraint couples to a distal end thereof relative to the clamp body.

3. The alignment guide of claim 2, wherein the distal end of the at least one lever arm comprises a position relatively higher than the patient-contacting interface selectively engaged with the ankle.

4. The alignment guide of claim 1, wherein the patient-contacting interface includes a pair of outwardly extending clamp arms generally forming a U-shaped enclosure for selectively receiving the ankle therein.

5. The alignment guide of claim 4, wherein the pair of outwardly extending clamp arms comprise an arcuate shape.

6. The alignment guide of claim 4, wherein the at least one lever arm comprises a pair of lever arms each upwardly extending from the pair of outwardly extending clamp arms.

7. The alignment guide of claim 6, wherein the restraint includes a first end selectively adjustably couplable with one of the pair of lever arms by way of a series of apertures formed within the restraint and a second end selectively adjustably coupled with the other of the pair of lever arms by a selectively lockable adjustment housing.

8. The alignment guide of claim 1, wherein the clamp body includes a casing housing a slide integrated therewith for selectively horizontally positioning the patient-contacting interface and the rod relative to the patient.

9. The alignment guide of claim 8, wherein the casing includes an externally accessible lock movable between a first unlocked position permitting movement of the slide relative to the casing and a second locked position in friction fit engagement with the slide thereby inhibiting movement of the slide relative to the casing.

10. The alignment guide of claim 1, wherein the at least one lever arm comprises an extendable lever arm.

11. The alignment guide of claim 1, wherein the restraint comprises a strap selected from the group consisting of an elastic strap, a rubber strap, a silicone strap, a plastic strap, a belt, and a metal spring.

12. The alignment guide of claim 1, further including a hinge coupling the rod to the clamp body, the hinge permitting pivoting movement of the rod relative to the clamp body.

13. The alignment guide of claim 1, wherein the rod comprises a telescoping rod.

14. The alignment guide of claim 1, wherein the restraint comprises a pair of spring-loaded clamping paddles positioned along the at least one lever arm.

15. An ankle clamp alignment guide, comprising:

a clamp body having a patient-contacting interface selectively engageable with an ankle of a patient;

a rod upwardly extending from the clamp body terminating in a cutting guide end distal from the patient-contacting interface, the rod comprising an upper portion defining an upper alignment post and a lower portion defining a lever arm; and a restraint selectively coupled to the lever arm below the upper alignment post, the lever arm extending up from the clamp body and positioned entirely above the patient-contacting interface, wherein tightening the restraint generates a moment near where the patient-contacting interface selectively engages the ankle, to self-bias the cutting guide end of the rod generally toward the patient.

* * * * *